United States Patent
Sarkar et al.

(12)

(10) Patent No.: US 6,544,773 B1
(45) Date of Patent: Apr. 8, 2003

(54) MICROBIAL PROCESS FOR DEGRADATION OF PCBS IN CLOPHEN A-50 USING A NOVEL MARINE MICROORGANISM, PSEUDOMONAS CH07

(75) Inventors: Anupam Sarkar, Goa (IN); Jaysankar De, Goa (IN); Ramaiah Nagappa, Goa (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/777,373

(22) Filed: Feb. 5, 2001

(51) Int. Cl.$^7$ .............................. C12N 1/20; B09B 3/00
(52) U.S. Cl. ................. 435/253.3; 435/262.5; 588/207
(58) Field of Search ........................ 435/253.3, 262.5; 588/207

(56) References Cited

U.S. PATENT DOCUMENTS 4,843,009 A * 6/1989 Bopp ..................... 435/253.3
5,516,688 A * 5/1996 Rothmel ................. 435/253.3

* cited by examiner

*Primary Examiner*—Herbert J. Lilling
(74) *Attorney, Agent, or Firm*—J. Harold Nissen; Myron Greenspan; Lackenbach Siegel

(57) ABSTRACT

A novel marine microorganism (Pseudomonas CH07) capable of degrading different congeners namely coplanar, sterically hindered and other chlorobiphenyls present in a technical grade PCBs (Clophen A-50); the aerobic bacterial strain, identified as Pseudomonas CH07 isolated from coastal zone of Arabian sea near Goa, India subjected to intense anthropogenic activity is shown to degrade PCBs of chlorine content (4–7 chlorine atoms per biphenyl).

31 Claims, 4 Drawing Sheets

Figure 1:
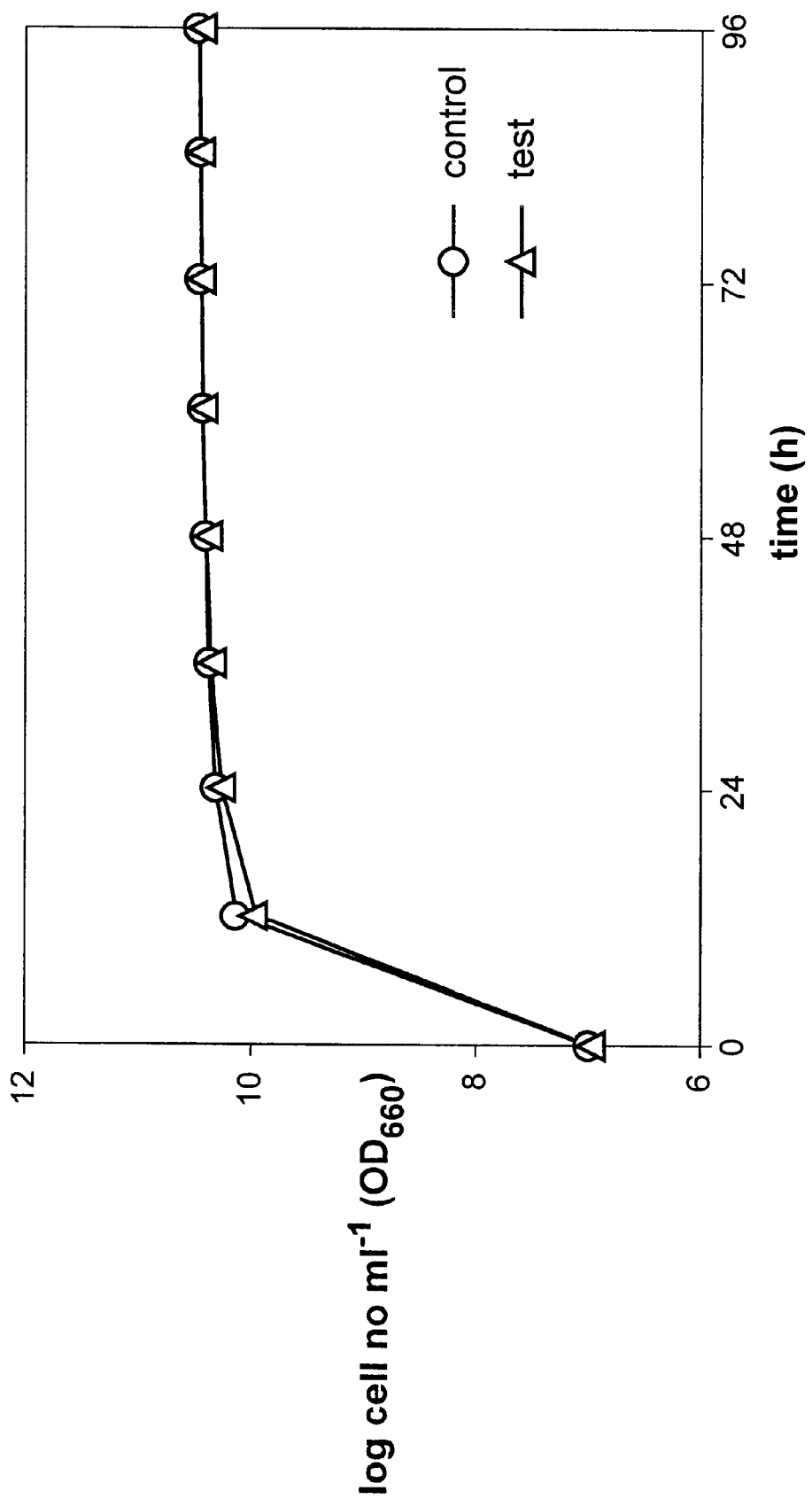

MICROBIAL PROCESS FOR DEGRADATION OF PCBS IN CLOPHEN A-50 USING A NOVEL MARINE MICROORGANISM, PSEUDOMONAS CH07

FILED OF THE INVENTION

The invention relates A novel marine microorganism (Pseudomonas CH07) isolated from the Indian coastal zone near Goa which is capable of biodegradation of PCBs including sterically hindered di and tri-ortho chlorinated biphenyls and coplanar congeners present in a technical grade Clophen A-50 (Bayer, Lot no. 16572) by the novel strain of marine microorganism, Pseudomonas CH07.

BACKGROUND OF THE INVENTION

Classification of PCBs

PCBs are non-volatile organic compounds (depending on the degree of chlorination they may belong to the class of semi volatile organic compounds (SVOC). PCBs are divided into two groups of isomers based on the difference in structure:

1. Coplanar PCBs—those compounds have chlorinated substituents in both para positions, and any/all meta positions. Meta or para chlorine substituents have, by their structure, low steric hindrance with neighboring H, which allows free rotation about the phenyl-phenyl bond. There are 20 coplanar PCBs, out of which three (77, 126, 105) are very toxic. Most importantly, they are non-ortho chlorinated.
2. Mono-ortho chlorinated PCBs-all molecules have one-chloro substitutions in the other positions only. Ortho substituents tend to create rigid bonds due to the large steric interference between Cl and H atoms.
3. Di-ortho a represents the chlorine atoms at the ortho-positions.
4. Tri-ortho represents the chlorine atom at the ortho-positions.

Depending on the number of Cl atoms on the biphenyl rings PCBs are divided into mono, di, tri, tetra, penta, hexa, hepta, octa, nona and deca-chlorobiphenyls and there are 209 possible PCBs theoretically but many do not occur because of steric hindrance.

Most abundant PCBs in commercial mixtures are ortho-substituted congeners, which are readily degradable. However, smaller amounts of the so-called 'di-oxin' like PCBs namely the coplanar (=non-ortho substituted) and mono-ortho substituted congeners, are present in the commercial mixture as well. Broad classification:

a) Non-ortho or mono-ortho chlorinated Biphenyls (coplanar).
b) Ortho-substituted chlorinated biphenyls.
c) Sterically hindered chlorinated Biphenyls.

Polychlorinated biphenyls (PCBs) represent a class of toxic xenobiotics that are distributed throughout the biosphere. Over the past several years, PCBs have received increasing attention due to accumulation of their residues in tissues of living organisms and biomagnified through the food chain leading to health hazards. PCBs are produced by direct chlorination of biphenyl. Due to the large number of hydrogen atoms present on the biphenyl nucleus, many different chlorinated compounds (termed "congeners" isomers of different homologous series) are possible. As many as 209 congeners of the PCBs could be theoretically produced [Furukawa, Biodegradtion and Detoxification of Environmental Pollutants, p. 34–57. CRC press. (1982)]; however, due to steric restrictions, only about half of this number are actually found in the environment. Therefore, PCBs are mixtures of a variety of chlorine-substituted biphenyl molecules. Clophen A-50 is a technical grade chemical compound containing about 40 different congeners of PCBs. Clophen is well known in commercial circles and to peoples skilled in the art. In fact, Clophen A-50 is equivalent to Aroclor 1256 i.e. it has about 56% chlorines w/w [Yadav; Jagjit S.; Reddy; C. A.; Quensen; John F.; Tiedje; James M. Degradation of polychlorinated biphenyl mixtures in soil using *Phanerochaete chrysosporium* in nutrient rich, non-ligninolytic conditions. U.S. Pat. No. 6,107,079. (Aug. 22, 2000)].

Due to their lipophilic and hydrophobic characteristics, the PCBs get accumulated in tissues of various species of organisms and are magnified through the food chain [Furukawa supra; Jacobson et al. Develop. Psychol. 20: p.523–532. (1984); Sarkar, A. and Everaarts, J. M. (1998) Riverine input of chlorinated hydrocarbons in the coastal Pollution. In: Ecology of Wetlands and Associated Systems. Ed. S. K. Majumdar, E. W. Miller and Fred J. Brenner. Chapter 27, Pub: Pennsylvania Academy of Science. pp, 400–423; Sarkar, A. (1994) Occurrence and distribution of persistent chlorinated hydrocarbons in the seas around India. In: The Oceans: Physico-chemical Dynamics and Resources (ed) S. K. Majumdar, E. W. Miller, G. S. Forbes, R. F. Schmalz and Assad, A. Panah. The Pennsylvania Academy of Science. Chapter-28,pp, 445–459.]. The physical effects of PCBs vary from mammals, to birds, to humans. Natural microbial populations do not easily remove PCBs. Some PCB congeners are found to be transformed by both anaerobic and aerobic bacteria [Abramowicz, D. A., Crit. Rev. Biotechnol. 10: 241–251. (1990)]. The aerobic degradation of PCBs is generally limited to less—chlorinated congeners (five or fewer chlorines per biphenyl molecule) by an enzymatic mechanism involving deoxygenation of the aromatic ring [Bedard, D. L., et al., Appl. Environ. Microbiol. 53: 1094–1102. (1987); Bradley; Clifford A.; Kearns; Robert D.; Wood; Pauline P.; Black; William E. Degradation of polyhalogenated biphenyl compounds with white-rot fungus grown on sugar beet pulp. U.S. Pat. No. 5,583,041 (Dec. 10, 1996); Sarkar, A. (1994) Comments on "Degradation of polychlorinated dibenzo-p-dioxin and dibenzo-furan contaminants in 2,4,5-T by photoassisted iron-catalyzed hydrogen peroxide" by J. J. Pignatello and L. Q. Huang. Wat. Res. Vol. 27: 1731–1736. Water Research. Vol: 28 No. 12, pp, 2589–2594. Sarkar, A. (1994) Comments on: "Evaluation of dechlorination mechanisms during anaeorobic fermentation of bleached kraft mill effluent", by W. J. Parker, E. R. Hall and G. J. Farquhar, Wat. Res. 27, 1269–1273 (1973). Water Research Vol. 28: No. 9, pp, 2043–2044, 1994.] The more chlorinated congeners are generally recalcitrant to aerobic degradation [Kimbara; Kazuhide; Shimura; Minoru; Hatta; Takahasi; Kiyohara; Hohzoh. Method for degrading polychlorinated biphenyls and novel microorganism. U.S. Pat. No. 5,897,996 (Apr. 27, 1999)]. In 1978, Furukawa and associates [Furukawa et al., Appl.Environ. Microbiol. 35:223–227. (1978)] studied the biodegradability of several isomers of PCBs. They found that as chlorine substitution increased, degradability decreased. An isomer with four Cl was not easily degraded. The position of the chlorine is also important. Ortho positioning of two chlorines on a single ring greatly inhibited degradation [MacFaddin, F. J. 1980.

Biochemical tests for identification of medical bacteria. Second edition. p. 527. Williams and Wilkins, Baltimore].

Considering the environmental importance of PCBs and the hazards posed by them, numerous investigators have been examining biological detoxification systems to deal with PCBs. One way to decipher the complexities of highly chlorinated isomers is to look into the problem, according to the order of the extent of chlorine substitution in the biphenyl ring. Of the 209 theoretically possible isomers and congeners of PCB, 20 members attain coplanarity due to non-ortho chlorine substitution in the biphenyl rings. In this group, three coplanar congeners such as 3,3,4,4'-tetrachlorobiphenyl, 3,3',4,4',5-pentachlorobiphenyl and 3,3',4,4'-pentachlorobiphenyls and 3,3',4,4',5,5'-hexachlorobiphenyls are approximate isostereomers of highly toxic 2,3,7,8-tetrachlorodibenzo-p-dioxin and 2,3,4,7,8-pentachlorodibenzofuran and hence elicit similar toxic and biologic responses typical of dioxins and furans [Safe, S.(1984) Polychlorinated biphenyls (PCBs) and polybrominated biphenyls (PBBs): biochemistry, Toxicology and mechanism of action. CRC Crit. Rev. Toxicol., 13, 319–93].

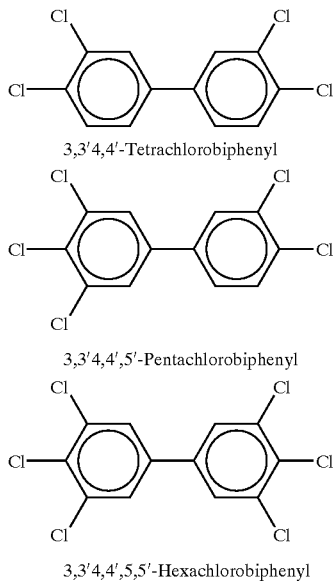

Because of the coplanarity, these three congeners of PCB were found to be most toxic chlorinated aromatic compounds in comparison with the rest of the congeners of PCBs [Yoshihara, S.; Nagata, K.; Yoshimura, H.; Kuroki, H. and Masuda, Y. (1981). Inductive effect on hepatic enzymes and acute toxicity of individual polychlorinated dibenzofuran congeners in rats. Toxicol. Appl. Pharmacol., 59, 580–588]. Several earlier studies indicate that toxic nature of technical PCB mixtures may be associated with the presence of trace levels of particular toxic PCB congeners having four or more chlorine atoms at both para and meta positions in the biphenyl rings but no chlorine atoms in ortho positions. [Yoshilhara, H., Ozawa, N. and Saeki, S. (1978). Inductive effect of polychlorinated biphenyl mixture and individual isomers on the hepatic microsomal enzymes. Chem. Pharmacol. Bull. (Tokyo), 26, 1215–21]

From structural point of view the physico-chemical properties of different conngeners of PCBs vary according to the positions of chlorine atoms in the biphenyl ring.

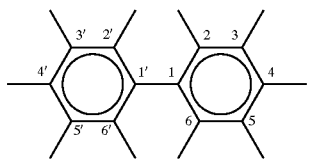

The substitution of chlorine atoms at the ortho positions (2,2' and 6,6') of the biphenyl rings clearly indicate the steric hindrance between them due to which the two aromatic rings of the biphenyl get distorted into non-planar configuration as shown below.

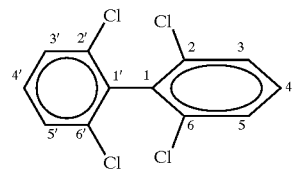

PCBs have widely been used industrially largely because of their versatile characteristics such as non-inflammability, hydrophobicity, thermal stability etc. Such physico-chemical properties of PCBs have made it highly useful as heat resistant compounds in the transformer and in other high-temperature applications. PCBs have also been used in plasticizers, heat transfer and capacitor systems, surface coatings, printing inks, carbonless duplication paper, and waxes [Barton and Marlene, R. Bacterial degradation of 4-chlorobiphenyl. U.S. Pat. No. 4,999,300. (Mar. 12, 1991)]. Clophen A-50 is a technical grade chemical compounds containing different congeners of PCBs. Clophen A-50 is almost equivalent to Aroclor 1256 (i.e. about 56% chlorines w/w). While industrial use of PCBs has been sharply restricted, significant quantities of PCBs are still being released into the environment from waste dumps [25. Sarkar, A. Shailaja, M. S. and Desa, E. (2000) Analysis of PCBs in waste oil samples. Sponsored (Central Pollution Control Board, New Delhi) Project Report no. NIO/SP-23/2000; Sarkar, A. Shailaja, M. S. and Desa, E. (1999) Analysis of PCBs in Environmental samples. Sponsored (Central Pollution Control Board, New Delhi) Project Report no. NIO/SP-21/99] and failure of old electrical equipment. PCB contamination has been observed in drinking water sediments [Boon, J. P., Everaarts, J. M., Kastoro, W. W., Razak, H., Sumanta, I., Sumarno, Nelissen, P. H., Stefels, J. and Hillebrand, M. Th. J. (1989). Cyclic organochlorines in epibenthic organisms from coastal water around East Java, Neth. J. of Sea Res. 23: 4, 427439. Boons, J. P., Van Zantvroot, M. B., Govaert, M. J. M. A. (1985). Organochlorines in benthic polychaetes (Nephtys spp.) and sediments from the southern North Sea. Identification of individual PCB components, Neth. J. of Sea Res. 19:2, 93–109], wastewater, foods and aquatic organisms and especially in fish.

OBJECTS OF THE INVENTION

The main object of the invention is to provide a novel marine bacterium Psedumonas CH07 which was deposited on Jul. 9, 2002 in the ARS Patent Culture Collection, Microbial Genomics and Bioprocessing Research Unit, National Center for Agricultural Utilization Research, 1825 N. University Street, Peoria, Ill., 61604, as NRRL B-30604, which strain having degrading properties of congeners and has been isolated from coastal zone of Arabian Sea.

Another object of the invention is to provide the stain capable of sustaining growth in medium containing 100-ppm final concentration of Clophen A-50. Still another object of the invention is to provide a microbial process for the degradation of PCBs present in Clophen A-50 using the marine bacterium. Yet, Another object of the invention is the degradation of congeners present in the Clophen A-50 using the marine bacterium Psedumonas CH07. Yet, another object of the invention is to provide a process for degradation of non-ortho or mono-ortho chlorinated biphenyls (coplanar), ortho-substituted chlorinated biphenyls and sterically hindered chlorinated biphenyls PCBs present in Clophen A-50 using the novel marine bacterium Psedumonas CH07.

SUMMARY OF INVENTION:

The applicants have isolated a marine bacterium of the genus Pseudomonas that is cable of degrading several congeners of chlorine content (4–7) to lesser chlorine containing congeners from a technical grade PCBs (Clophen A-50). The present invention comprises a biologically pure strain of the genus Pseudomonas having the characteristics stated in the table1. The present invention is used to degrade the technical grade PCBs (Clophen A-50) and similar kind of chemicals for biodegradation of deadly PCBs. This strain is capable of sustaining growth in medium containing 100-ppm final concentration of Clophen A-50.

DETAILED DESCRIPTION OF THE INVENTION

Accordingly, the present invention provides a novel marine bacterium, Pseudomonas CH07, which was deposited in the depository at National Institute of Oceanography, Dona Paula, Goa 403004, India, and available to the public since Apr. 2, 2000, which strain is used for degradation of several/different congeners of PCBs contained in Clophen A-50 based on its unique properties.

The novel strain of marine microorganism designated as Pseudomonas CH07 is capable of degrading several congeners of PCB namely tetra-chlorobiphenyls, pentachlorobiphenyls, hepta-chlorobiphenyls containing 4–7 chlorine atoms on the biphenyl ring, sterically hindered di, tri-ortho chlorinated biphnyls and coplanar congeners of PCB.

In an embodiment of the present invention, the bacterium degrades non-ortho or mono-ortho chlorinated biphenyls (coplanar).

In another embodiment of the present invention, the bacterium degrades ortho-substituted chlorinated biphenyls.

In another embodiment of the present invention, the bacterium degrades sterically hindered chlorinated biphenyls.

In still another embodiment of the present invention, the bacterium degrades most of the congeners present in Clophen A-50 either its single or multiple congeners.

In an embodiment of the present invention, the bacterium degrades the congeners of PCB are selected from tetra-chlorobiphenyls, pentachlorobiphenyls, hexachloro biphenyls and hepta-chlorobiphenyls containing 4–7 chlorine atoms on the biphenyl ring, sterically hindered di, tri-ortho chlorinated biphenyls and coplanar congeners of PCB.

Yet another embodiment of the invention, the bacterium is used to detoxify Clophen A-50 and its constituent congeners of PCB when present at or equal to 100 ppm level.

Yet another embodiment of the invention, the bacterium is capable of degrading six sterically hindered di-ortho chlorinated biphenyls (cb-101, cb-97, cb-141, cb-138, cb-128 and cb-180).

Yet, another embodiment of the invention, the bacterium is capable of degrading two of the three most toxic coplanar PCBs in Clophen A-50.

Yet another embodiment of the invention, the bacterium degrades the PCBs present in Clophen A-50 within a short period of 40 hours.

Yet another embodiment, the bacterium culture used to degrade toxic PCBs present in Clophen A-50 is in the range between10 $\mu l$ to 50 $\mu l$.

Yet another embodiment, the bacterium degrades 20 to 100% of PCBs present in Clophen A-50.

In one more embodiment of the present invention, the microbial process for the degradation of PCBs present in Clophen A-50 comprising culturing the marine bacterium Pseudomonas CH07 and treating the PCBs with the bacterium for degrading congeners present in Clophen A-50.

In yet another embodiment, the bacterium Pseudomonas CH07 degrades non-ortho or mono-ortho chlorinated biphenyls (coplanar), ortho-substituted chlorinated biphenyls and sterically hindered chlorinated biphenyls PCBs present in Clophen A-50.

In yet another embodiment, PCBs are degraded substantially within a short period of 40 hours.

In yet another embodiment, the congeners of PCB degraded are selected from tetra-chlorobiphenyls, pentachlorobiphenyls, hexachlorobiphenyls and heptachlorobiphenyls containing 4–7 chlorine atoms on the biphenyl ring, sterically hindered di, tri-ortho chlorinated biphenyls and coplanar congeners of PCB.

In yet another embodiment, tetra chloro biphenyls present in Clophen A-50 is degraded by this bacterium.

In yet another embodiment, seven pentachloro biphenyls present in Clophen A-50 are degraded.

In yet another embodiment, four hexachlorobiphenyls present in Clophen A-50 are degraded.

In yet another embodiment, two heptachlorobiphenyls present in Clophen A-50 are degraded.

In yet another embodiment, the bacterium degrades the PCBs at a concentration ranging between 10 $\mu l$ to 50 $\mu l$.

In yet another embodiment, the bacterium degrades 20 to 100% of PCBs present in Clophen A-50.

In yet another embodiment, the bacterium is used to detoxify Clophen A-50 and its constituent congeners of PCB when present at or equal to 100-ppm level.

In yet another embodiment, the bacterium is isolated from marine environment and not altered genetically, and can be employed in situations at experimental pilot and at commercial scales, wherever there are marine conditions.

In yet another embodiment, the bacterial strain is capable of degrading six sterically hindered di-ortho chlorinated biphenyls (cb-101, cb-97, cb-141, cb-138, cb-128 and cb-180).

In yet another embodiment, two sterically hindered tri-ortho chlorinated biphenyls (cb-151 and cb-181) are degraded.

In yet another embodiment, the sterically hindered congeners are degraded by this organism under marine condition.

In yet another embodiment, different congeners of PCBs present in Clophen A-50, two congeners (CB-126, CB-181) get completely degraded.

In yet another embodiment, the congener cb-126 is completely degraded in about 40 hours.

In yet another embodiment, the marine bacterium is the most potent for degradation of two of the three most toxic coplanar PCBs in Clophen A-50.

In yet another embodiment, the organism is capable of degrading PCB congeners, cb-126 and cb-77 under marine condition.

In yet another embodiment, the coplanar PCB (3,3',4,4'-tetrachlorobiphenyl) is degraded very substantially within a short period of 40 hours.

BRIEF DESCRIPTION OF THE FIGURES AND THE TABLES

FIG. 1. Growth curve of Pseudomonas CH07 in presence of 100 ppm Clophen A-50 in 50% seawater nutrient broth.

Figure 2:
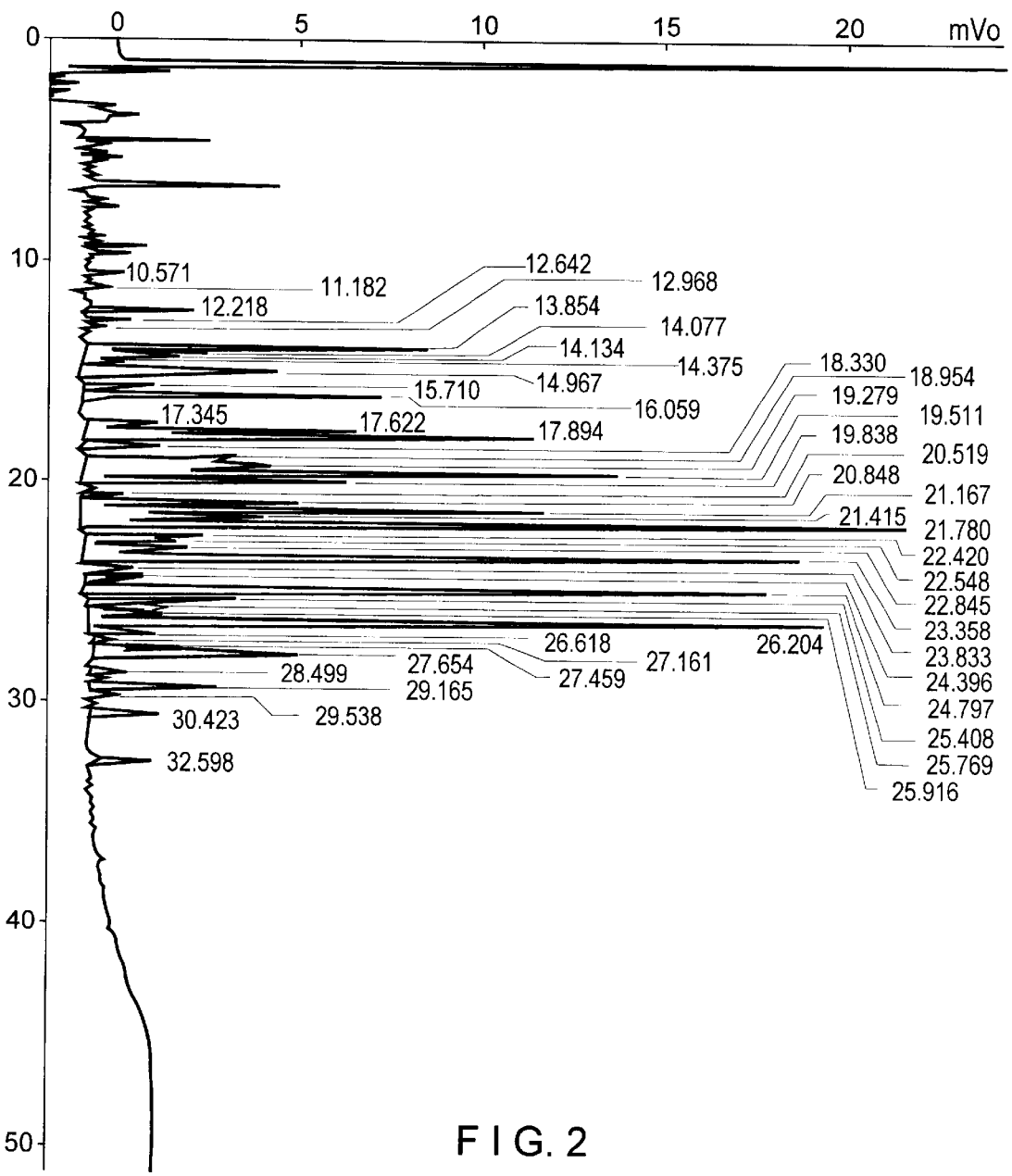

FIG. 2. Gas Chromatogram of Clophen A-50

Figure 3:
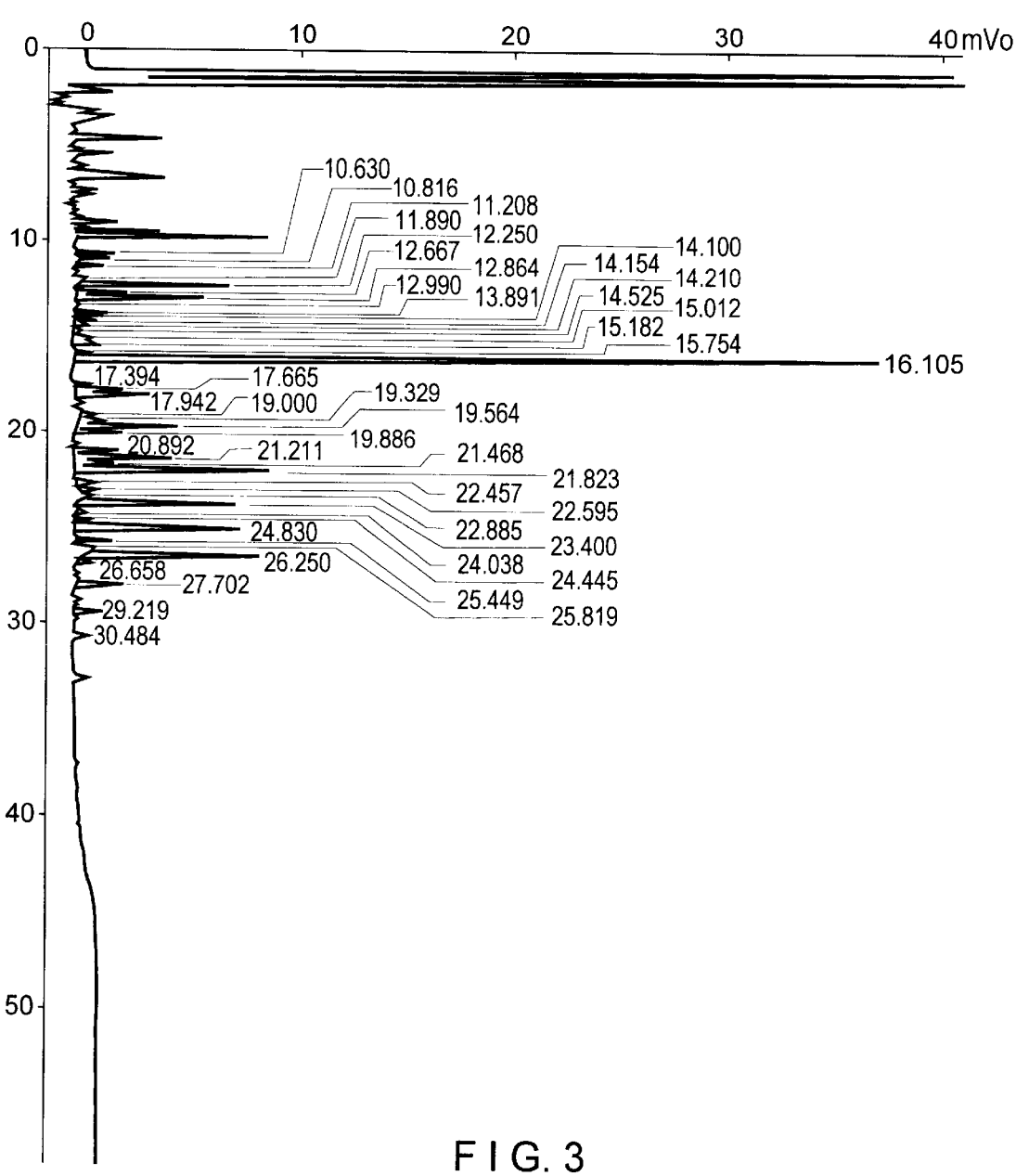

FIG. 3. Gas chromatogram of control at '0' hour.

Figure 4:
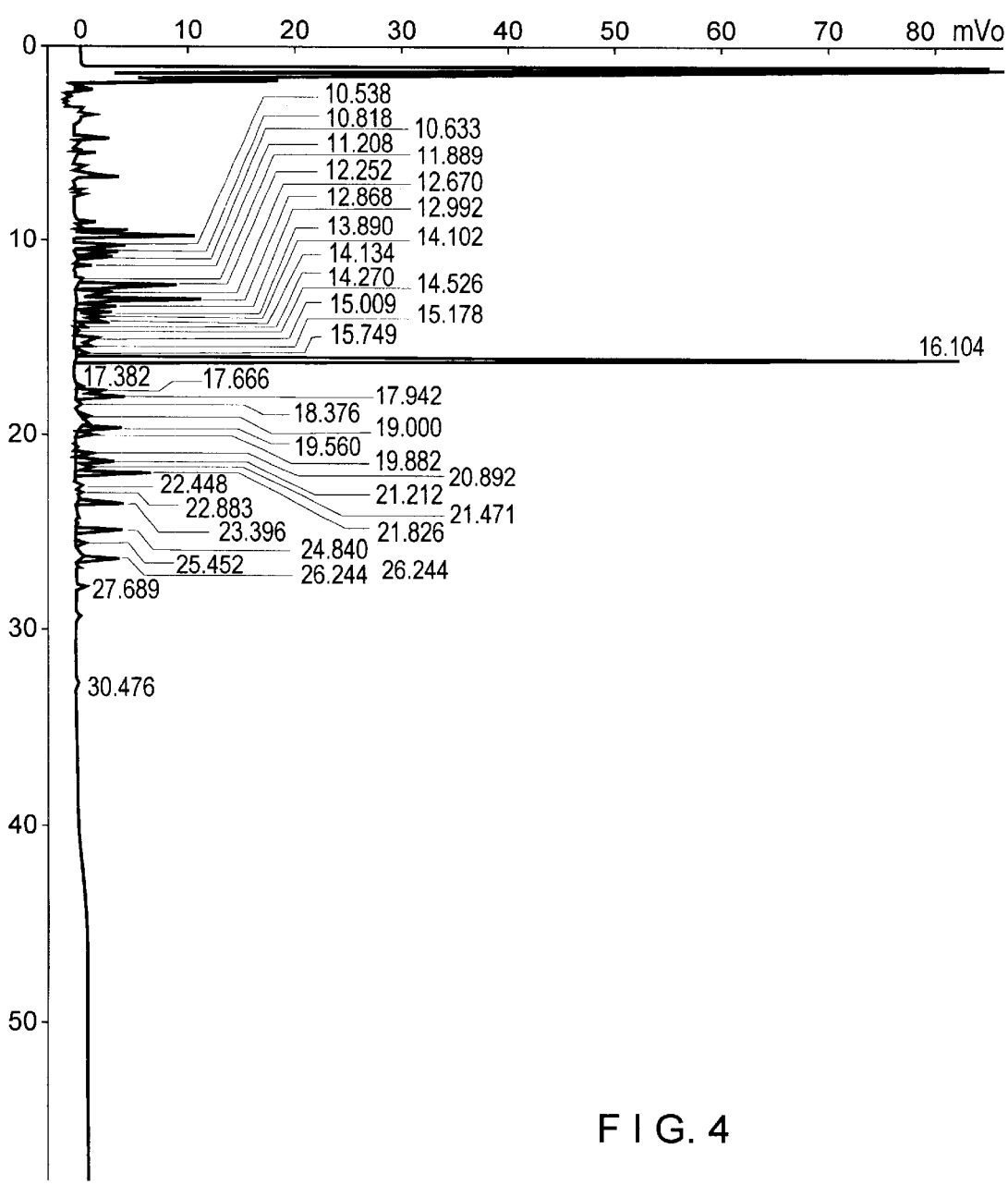

FIG. 4. Gas chromatogram of sample at '40' hour.

Table 1: Taxonomical characteristics of the microorganism Pseudomonas CH07

Table 2a: Percent degradation of PCBs (Clophen A-50) by Pseudomonas CH07.

Table 2b: percent degradation of coplanar congeners of PCBs (Clophen A-50) by Pseudomonas CH07.

Table 2c: Percent degradation of sterically hindered PCBs in Clophen A-50 by Pseudomonas CH07.

Table 3a: Structural characteristics of degraded congeners of PCBs and their Cl %

Table 3b: Structural characteristics of degraded coplanar congeners of PCBs and their Cl content %

Table 3c: Structural characteristics of degraded congeners of PCBs and their Cl

Table 4: Experimental conditions of the GC for analysis of PCBs in the sample extracts.

A novel strain of marine microorganism designated as Pseudomonas CH07 is capable of degrading several congeners of PCB namely tetra-chlorobiphenyls, pentachlorobiphenyls, hepta-chlorobiphenyls containing 4–7 chlorine atoms on the biphenyl ring, sterically hindered di, tri-ortho chlorinated biphnyls and coplanar congeners of PCB.

Isolation of the Microorganism

The microorganism identified as Pseudomonas sp was isolated from a water sample collected from a coastal zone subjected to intense anthropogenic activity following routine microbiological methods. Many isolates were randomly selected and purified for further studies. Once purified, the isolate was tested for growth on seawater nutrient agar containing Clophen A-50 to a final concentration of 10, 50 and 100 ppm and once grown, the bacterium was grown in quantity for identification and experimentation.

Identification

To characterize the isolate, several biochemical tests were carried out. Presence of various enzymes viz. lipase, gelatinase, amylase, oxidase, catalase, and urease, decarboxylases (Arginine and Ornithine) was examined. Utilization of gluconate, pyruvate, citrate, and cellobiose, utilization of glucose, sucrose, mannitol, arabinose, rhamnose, nitrate reduction, MR (methyl red), VP (Voges Proskaeur), $H_2S$ production and oxidation-fermentation was examined by following the method as described by MacFaddin. The isolate was identified to its genus level following Bergey's Manual of Systematic Bacteriology and Oliver's scheme for identification of gram-negative marine bacteria. The results of the tests for the identification are shown in the table 1.

TABLE 1

Taxonomical characteristics of the microorganism Pseudomonas CH07

| Test | Response |
|---|---|
| Gram stain | –ve |
| Shape | Very small rod |
| Motility | +** |
| Pigment | Fluorescent green |
| Oxidase | Slow reaction |
| OF | No reaction |
| Gelatinase | + |
| Catalase | ++*** |
| Lipase | – |
| Starch hydrolysis | + |
| Arginine | + |
| Omithin | – |
| VP | – |
| MR | – |
| Nitrate reduction | ++ |
| $H_2S$ | –* |
| Indole | – |
| Urease | – |
| Growth on | |
| Citrate | + |
| Sucrose | Alkaline |
| Mannitol | Acidic |
| Rhamnose | Acidic |
| Arabinose | Alkaline |
| Streptomycin | ++ |
| Tetracycline | ++ |
| Demechlocyclin | ++ |
| Kanamycin | ++ |
| Neomycin | ++ |

*negative response (no growth), positive response (slight or moderate growth) *very good response (good growth).

Culture Media & Experimental Methods

A defined seawater nutrient broth medium (code no. 088 from Himedia, Bombay) containing beef extract 3 g $L^{-1}$, peptic digest of animal tissue 5 g $L^{-1}$ was used. One liter of medium contained 500 ml seawater and 500 ml distilled water and the final pH was adjusted to 7 using 0.1 N NaOH. After autoclaving, the required amount of stock solution (10,000 ppm) of Clophen A-50 was added to the medium in sterile condition to achieve a final concentration of 100 ppm. Immediately after adding the stock PCBs solution, the hexane part of it was evaporated out by gently swirling the flask in sterile condition and sterile glycerol was added to the medium in a 1:1 ratio of stock solution:glycerol. 40 $\mu$l of 24 hold culture of Pseudomonas CH07 growths was added in two replicates of 20 ml of test (seawater nutrient broth+ Clophen A-50) medium to seawater nutrient broth (without any addition of Clophen A-50). Controls in duplicate were also maintained without the addition of the organism at room temperature (ca. 28°±2° C.). Control and test cultures were maintained at room temperature for two days and at various predecided intervals of time, the samples was taken out aseptically and prepared for GC analysis. The details of the sample preparation is described below.

Analytical Procedure

The PCBs were analyzed following the method described by Boon et al. The method was standardized in our laboratory using the PCBs standards obtained from Promochem, Germany as well as other analytical grade chemicals from E. Merck. The purity of the solvents was checked by Gas chromatography for each of the bottles. The different adsorbents, alumina, silica, were purified by soxhlet extraction with di-chloro-methane (HPLC grade) for about eight hours. The anhydrous $Na_2SO_4$ and the glass wool were also purified by Soxhlet extraction with HPLC grade di-chloro methane. The different steps of the analytical methods are illustrated below:

Various Steps Followed for Preparation of Reagents for Extraction of PCBs:
i. Distill n-hexane
ii. Check the purity of the solvent by injecting into the G.C.
iii. Distill acetone.
iv. Check the purity of the solvent by injecting only 0.1 $\mu$l into the G.C.
v. Distill dichloromethane
vi. Check the purity of the solvent by injecting only 0.1 $\mu$l into the G.C.
vii. Distill milliQ water.
viii. Purify alumina by Soxhlet extraction with bi-distilled dichloromethane for 8 hrs.
ix. Activate purified alumina
x. Deactivate activated alumina by 10% with bi-distilled water.
xi. Check the purity of the alumina
xii. Purify silica with soxhlet extraction for 8 hours
xiii. Activate purified silica
xiv. Deactivate silica by 5% using bidistilled water
xv. Check the purity of silica Extraction of PCBs from the Sample:
i. Aliquot of 1 ml sample was treated with 1 ml n-hexane (HPLC grade) thrice and thoroughly mixed by a vortex mixture for five minutes each time. The upper part of the solvent layer (solvent extract) was separated with the help of micropipette and transferred to a sterilized glass tube.
ii. Concentrate the solvent extract to 1 ml by evaporation with Snyder column evaporator on a water bath at 85° C.
iii. Purify of the solvent extract by alumina clean up using micro-column technique.
iv. Concentrate the solvent extract to 1 ml by evaporation with Snyder column evaporator on a water bath at 85° C.
v. Isolate PCBs from polar chlorinated compounds by eluting through micro-column of silica.
vi. Concentrate the PCBs fraction to 1 ml by evaporation with Snyder column evaporator on a water bath at 85° C.
vii. Analyze the aliquot by GC-ECD with reference to standard PCBs (individual congeners).

Gas Chromatographic Analysis of PCBs

The samples were analyzed by gas chromatography (Varian GC-3380) coupled with an electron capture detector and an autosampler 8200. Capillary column VA-5 (30 m×0.25 mm) was employed with electron capture detector (EID) for peak detection. Argon with 5% methane was the carrier gas. A temperature program was used (table. 3). Injector temperature was 250° C. with rare exceptions, these conditions yielded peaks that were well defined and well separated. The experimental condition of the instrument is illustrated in the table-4. The analysis of PCBs was calibrated using the standards for individual congeners of PCBs obtained from Promochem, Germany. Using different dilutions of the stock solution of the standards carried out the calibration of each of the individual congeners. The linearity of the calibration curve was determined with a range of dilution of the mix-standards. The concentrations of different congeners of PCBs in different samples and their identifications are shown in the chromatographic report and the chromatograms for each of the samples.

Degradation Mechanism of PCBs

Microbial detoxification of PCBs begins with dechlorination. This involves the stepwise removal of Cl atoms and their replacement with hydrogen atoms. However, most naturally occurring microbially mediated dechlorination process exhibit limited specificity. From the literature, it is increasingly clear that the dechlorination is generally restricted to removal of para- or meta-chlorines located adjacent to other chlorines, hence residual meta- and/or para-chlorines remain. In natural and genetically non-altered microorganisms the extensive and desirable removal of all meta- and para-chlorines does not occur, and the end products contain 3-; 2,5-; and 2,3,5-chlorophenyl groups or 4-, 2,4-, and 2,4,6,-chlorophenyl groups.

Chemical transformation can occur through biodegradation of PCB mixtures in the environment. Dechlorination is not synonymous with detoxification, as congeners having carcinogenic activity can be formed through oxidation. PCBs with higher Cl content are extremely resistant to oxidation and hydrolysis. From this perspective the unique characteristics of CH07 we have isolated from the marine environment are noteworthy. In that, this strain has exhibited its ability to degrade two of the three coplanar PCB congeners which are the most toxic of all the PCB congeners.

The applicants hypothesize that the biodegradation of PCBs by the exclusively aerobic CH07 may occur via aerobic respiration involving reaction with mono- and dioxygenase; in a final step $H_2O$ will be incorporated onto the biphenyl ring.

In principle, bacteria cannot use chlorinated aromatic hydrocarbons as their nutritional substrates. From the literature, it is well known that bacteria growing on non-chlorinated biphenyl are capable to cause chemical reactions on the chlorinated ring system as well. However, some microorganisms are capable to use lower chlorinated PCBs as C-source. The aerobic biodegradation of PCBs is generally limited to less-chlorinated congeners ($\geqq 5$ Cl atoms per biphenyl ring) by a mechanism involving deoxygenase attack of the aromatic ring. In general, formation of chlorinated benzoic acids is the major degradation pathway for PCBs and the applicants suggests such endproduct formation by Pseudomonas CH07.

Although increasing number of chlorine substituents decreases biodegradation of PCBs, the potential of Pseudomonas CH07 to attack chlorobiphenyls having $\geqq 5$ Chlorine atoms is very important in the degradation and detoxification process of both sterically hindered and coplanar classes of PCBs.

Growth Curves

The growth rate of the isolate was determined in seawater nutrient broth (SWNB). 50 $\mu$l of a twenty-four hour old culture of Pseudomonas isolate (CH07) was inoculated into two 250 ml flasks containing SWNB (100 ml) with Clophen A-50 added to them to a final concentration of 100 ppm. In two other flasks containing the same SWNB without any addition of the PCBs similar amount of inoculum was added. The flasks were incubated on a rotary shaker (200-RPM) at room temperature (ca. 28°±2° C.) for 120 hour. The absorbance ($OD_{660}$) of culture was measured every 12 h. Cell numbers were calculated from $OD_{660}$ by spread plating aliquots of 12 h old culture with a corresponding $OD_{660}$ SWNB. It was determined that one OD corresponds to ca.$1\times10^{10}$ cells $ml^{-1}$. Log values of cell numbers were plotted to draw growth curves (FIG. 1).

FIG. 1 clearly shows that there is no appreciable change or effect on the growth of Pseudomonas CH07. Thus, the effectiveness of the bacterium in degrading different congeners of PCBs in Clophen A-50 has been clearly substantiated. Most importantly, highly chlorinated congeners, CB-180 and CB-181 were found to be degraded sufficiently.

The extent of degradation of different congeners of PCBs in presence of other chlorobiphenyls is a clear indication that this bacterium can be used effectively for their detoxification.

pH Measurement pH of the medium were measured by pH Analyzer [(model: Elico (India) LI 612].

Measurement of Optical Density

Cell growths in seawater nutrient broths were determined using a spectrophotometer [model: Shimadzu, UV-1201 V].

Vortex

The extraction of PCBs from the samples was performed with n-hexane using a vortex mixer [model: Eltek® Vortex Mixer; VM301]

Chemicals

Chemicals used were as follows: Clophen A-50, lot no. 16572 from Bayer, Germany; n-hexane (OMNISOLV-UN 1208, lot no. 39319. CAS-110-543), acetone (LICKROSOLV-UN 1090, batch no. T A9 T4815384), dichloromethane (LICHROSOLV-UN 1593, batch no. 17 14426), Anhydrous Sodium sulfate, Alumina, and Silica from E-Merck Ltd., Germany & India; glycerol (AR grade, product no. G 0010, batch no. 6 GCV0696) from Ranbaxy Laboratories ltd., India and nutrient broth (M008, batch no. 8E 118) from Himedia Laboratories Pvt. ltd., India.

TABLE 2a

Percent degradation of PCBs by Pseudomonas CH07

| Chlorobiphenyls | Molecular Formula | Conc. of PCBs in Control (ng/ml) | Conc. of PCBs in Test sol. (incubation) 40 hrs. (ng/ml) | Degradation Of PCBs (%) |
|---|---|---|---|---|
| CB-101 (2,2',4,5,5'-Pentachloro) | $C_{12}H_5Cl_5$ | 18.17 | 14.50 | 20.19 |
| CB-119 (2,3',4,4',6-Pentachloro) | $C_{12}H_5Cl_5$ | 8.07 | 6.48 | 19.66 |
| CB-97 (2,2',3',4,5-Pentachloro) | $C_{12}H_5Cl_5$ | 8.17 | 6.57 | 19.69 |
| CB-116 (2,3,4,5,6-Pentachloro) | $C_{12}H_5Cl_5$ | 10.09 | 8.06 | 20.04 |
| CB-77 (3,3',4,4'-Tetrachloro) | $C_{12}H_6Cl_4$ | 53.37 | 40.42 | 24.25 |
| CB-151 (2,2',3,5,5',6-Hexachloro) | $C_{12}H_4Cl_6$ | 2.04 | 1.28 | 37.32 |
| CB-118 (2,3',4,4',5-Pentachloro) | $C_{12}H_5Cl_5$ | 1.31 | 0.77 | 40.72 |
| CB-105 (2,3,3',4,4'-Pentachloro) | $C_{12}H_5Cl_5$ | 17.54 | 9.29 | 46.69 |
| CB-141 (2,2',3,4,5,5'-Hexachloro) | $C_{12}H_4Cl_6$ | 3.57 | 1.59 | 55.38 |
| CB-138 (2,2',3,4,4',5'-Hexachloro) | $C_{12}H_4Cl_6$ | 1.62 | 0.71 | 55.97 |
| CB-126 (3,3',4,4',5-Pentachloro) | $C_{12}H_5Cl_5$ | 2.75 | 00.00 | 100 |
| CB-128 (2,2',3,3',4,4'-Hexachloro) | $C_{12}H_4Cl_6$ | 5.02 | 1.79 | 64.33 |
| CB-181 (2,2',3,4,4',5,6-Heptachloro) | $C_{12}H_3Cl_7$ | 2.87 | 00.00 | 100 |
| CB-180 (2,2',3,4,4',5,5'-Heptachloro) | $C_{12}H_3Cl_7$ | 1.64 | 0.63 | 61.33 |
| Total conc. (ng/ml) | | 163.23 | 92.09 | 32.29 |

TABLE 2b

Percent degradation of coplanar congeners of PCBs by microorganisms, Pseudomonas CH07

| Sr. No. | Chlorobiphenyls | Molecular Formula | Conc. Of PCBs in Control (ng/ml) | Conc. of PCBs in Test sol. (incubation) 40 hrs. (ng/ml) | Degradation Of PCBs (%) |
|---|---|---|---|---|---|
| 1 | CB-77 (3,3',4,4'-Tetrachloro) | $C_{12}H_6Cl_4$ | 53.37 | 40.42 | 24.25 |
| 2 | CB-126 (3,3',4,4',5-Pentachloro) | $C_{12}H_5Cl_5$ | 2.75 | 00.00 | 100 |

TABLE 2c

Percent degradation of PCBs by a marine microorganism, Pseudomonas CH07

| Sr. No. | Chloro-biphenyls | Molecular Formula | Conc. of PCBs in Control (ng/ml) | Conc. of PCBs in Test sol. (incubation) 40 hrs. (ng/ml) | Degradation Of PCBs (%) |
|---|---|---|---|---|---|
| 1 | CB-101 (2,2',4,5,5'-Pentachloro) | $C_{12}H_5Cl_5$ | 18.17 | 14.50 | 20.19 |
| 2 | CB-97 (2,2',3',4,5-Pentachloro) | $C_{12}H_5Cl_5$ | 8.17 | 6.57 | 19.69 |
| 3 | CB-151 (2,2',3,5,5',6-Hexachloro) | $C_{12}H_4Cl_6$ | 2.04 | 1.28 | 37.32 |
| 4 | CB-141 (2,2',3,4,5,5'-Hexachloro) | $C_{12}H_4Cl_6$ | 3.57 | 1.59 | 55.38 |
| 5 | CB-138 (2,2',3,4,4',5'-Hexachloro) | $C_{12}H_4Cl_6$ | 1.62 | 0.71 | 55.97 |
| 6 | CB-128 (2,2',3,3',4,4'-Hexachloro) | $C_{12}H_4Cl_6$ | 5.02 | 1.79 | 64.33 |
| 7 | CB-181 (2,2',3,4,4',5,6-Heptachloro) | $C_{12}H_3Cl_7$ | 2.87 | 00.00 | 100 |
| 8 | CB-180 (2,2',3,4,4',5,5'-Heptachloro) | $C_{12}H_3Cl_7$ | 1.64 | 0.63 | 61.33 |

TABLE 3a

Structural Characteristics of PCBs degraded by Pseudomonas CH07

| Chlorobiphenyls | Molecular Formula | Mol. Wt. | Cl (%) | Structures |
|---|---|---|---|---|
| CB-101 (2,2',4,5,5'-Pentachloro) | $C_{12}H_5Cl_5$ | 254.5 | 69.74 | 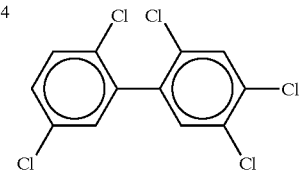 |
| CB-119 (2,3',4,4',6-Pentachloro) | $C_{12}H_5Cl_5$ | 254.5 | 69.74 | 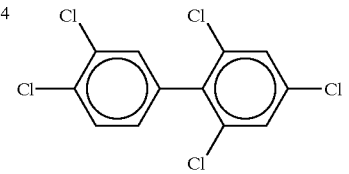 |
| CB-97 (2,2',3',4,5-Pentachloro) | $C_{12}H_5Cl_5$ | 254.5 | 69.74 | 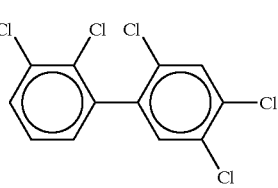 |

TABLE 3a-continued

Structural Characteristics of PCBs degraded by Pseudomonas CH07

| Chlorobiphenyls | Molecular Formula | Mol. Wt. | Cl (%) | Structures |
|---|---|---|---|---|
| CB-116 (2,3,4,5,6-Pentachloro) | $C_{12}H_5Cl_5$ | 254.5 | 69.74 | 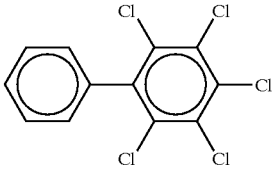 |
| CB-77 (3,3',4,4'-Tetrachloro) | $C_{12}H_6Cl_4$ | 220 | 64.54 | 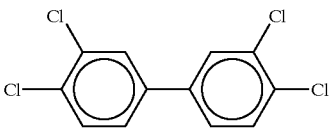 |
| CB-151 (2,2',3,5,5',6-Hexachloro) | $C_{12}H_4Cl_6$ | 289 | 73.70 | 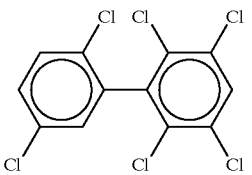 |
| CB-118 (2,3',4,4',5-Pentachloro) | $C_2H_5Cl_5$ | 254.5 | 69.74 | 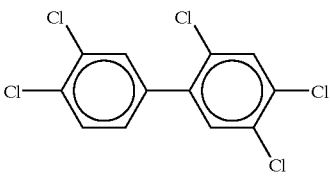 |
| CB-105 (2,3,3',4,4',-Pentachloro') | $C_{12}H_5Cl_5$ | 254.5 | 69.74 | 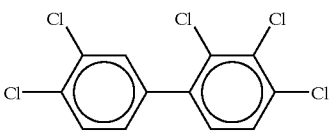 |
| CB-141 (2,2',3,4,5,5'-Hexachloro) | $C_{12}H_4Cl_6$ | 289 | 73.70 | 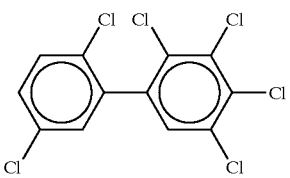 |
| CB-138 (2,2',3,4,4',5'-Hexachloro) | $C_{12}H_4Cl_6$ | 289 | 73.70 | 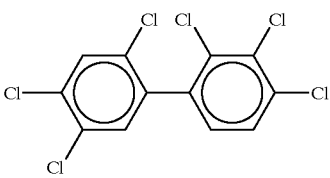 |
| CB-126 (3,3',4,4',5-Pentachloro) | $C_{12}H_5Cl_5$ | 254.5 | 69.74 | 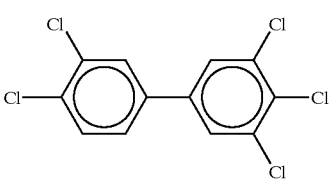 |
| CB-128 (2,2',3,3',4,4'-Hexachloro) | $C_{12}H_4Cl_6$ | 289 | 73.70 | 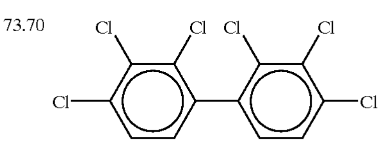 |

TABLE 3a-continued

Structural Characteristics of PCBs degraded by Pseudomonas CH07

| Chlorobiphenyls | Molecular Formula | Mol. Wt. | Cl (%) | Structures |
|---|---|---|---|---|
| CB-181 (2,2',3,4,4',5,6-Heptachloro) | $C_{12}H_3Cl_7$ | 323.5 | 76.81 | 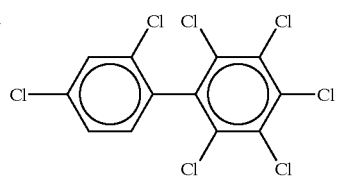 |
| CB-180 (2,2',3,4,4',5,5'-Heptachloro) | $C_{12}H_3Cl_7$ | 323.5 | 76.81 | 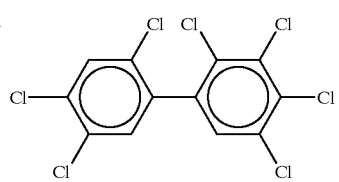 |

TABLE 3b

Structural characteristics of the coplanar congeners of PCBs degraded by micro-organisms, Pseudomonas CH07

| Sr. No. | Chlorobiphenyls | Molecular Formula | Mol. Wt. | Cl (%) | Structures | Coplanarity |
|---|---|---|---|---|---|---|
| 1 | CB-77 (3,3',4,4'-Tetrachloro) | $C_{12}H_6Cl_4$ | 220 | 64.54 | 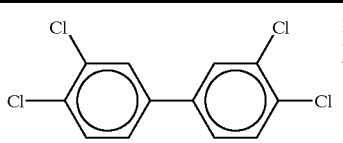 | Non-ortho tetrachloro biphenyl |
| 2 | CB-126 (3,3',4,4',5-Pentachloro) | $C_{12}H_5Cl_5$ | 254.5 | 69.74 | 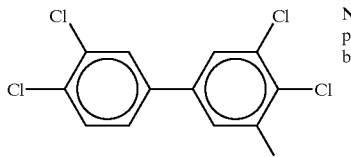 | Non-ortho pentachloro biphenyl |

TABLE 3c

Structural characteristics of sterically hindered congeners of PCBs degraded by a marine micro organisms Pseudomonas CH07

| Sr No. | Chlorobiphenyls | Molecular Formula | Mol. Wt. | Cl (%) | Structures | Ortho position of chlorine |
|---|---|---|---|---|---|---|
| 1 | CB-101 (2,2',4,5,5'-Pentachloro) | $C_{12}H_5Cl_5$ | 254.5 | 69.74 | 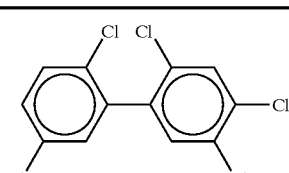 | Di-ortho |

TABLE 3c-continued

Structural characteristics of sterically hindered congeners of PCBs
degraded by a marine micro organisms Pseudomonas CH07

| Sr No. | Chlorobiphenyls | Molecular Formula | Mol. Wt. | Cl (%) | Structures | Ortho position of chlorine |
|---|---|---|---|---|---|---|
| 2 | CB-97 (2,2',3',4,5-Pentachloro) | $C_{12}H_5Cl_5$ | 254.5 | 69.74 | 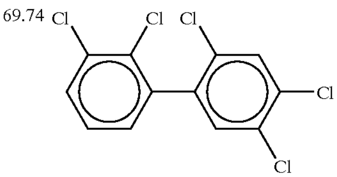 | Di-ortho |
| 3 | CB-151 (2,2',3,5,5',6-Hexachloro) | $C_{12}H_4Cl_6$ | 289 | 73.70 | 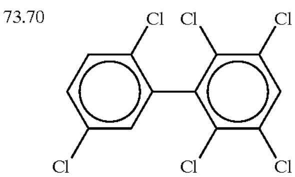 | Tri-ortho |
| 4 | CB-141 (2,2',3,4,5,5'-Hexachloro) | $C_{12}H_4Cl_6$ | 289 | 73.70 | 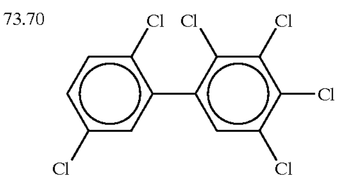 | Di-ortho |
| 5 | CB-138 (2,2',3,4,4',5'-Hexachloro) | $C_{12}H_4Cl_6$ | 289 | 73.70 | 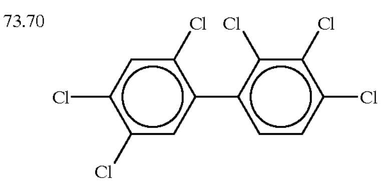 | Di-ortho |
| 6 | CB-128 (2,2',3,3',4,4'-Hexachloro) | $C_{12}H_4Cl_6$ | 289 | 73.70 | 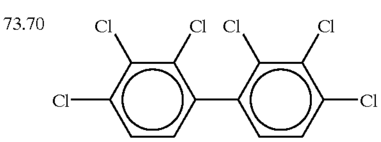 | Di-ortho |
| 7 | CB-181 2,2',3,4,4',5,6-Heptachloro | $C_{12}H_3Cl_7$ | 323.5 | 76.81 | 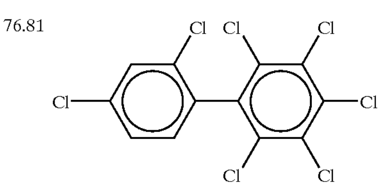 | Tri-ortho |
| 8 | CB-180 (2,2',3,4,4',5,5'-Heptachloro) | $C_{12}H_3Cl_7$ | 323.5 | 76.81 | 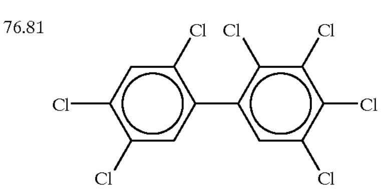 | Di-ortho |

TABLE 4

Experimental conditions of the GC for analysis of PCBs in the sample extracts

| Instrument | Gas chromatograph (Varian GC-3380) with auto sampler 8200 |
|---|---|
| Detector | 1079 ECD (Electron Capture Detector) (Ni$^{63}$) |
| Column | Capillary column VA-5 (30 m × 0.25 mm) |
| Carrier gas | Argon with 5% methane |
| Make up gas | Argon with 5% methane |
| Gas pressure | 25 PSI |
| Equilibration time | 1 min |
| Injector temperature | 250° C. |
| Detector temperature | 340° C. |
| Column temperature | Initial 110° C. for 2 min. |
| Ramp rate | 10° C. per min |
| 2$^{nd}$ oven temperature | 180° C. for 8 min |
| Ramp rate | 4° C. per min |
| 3$^{rd}$ oven temperature | 220° C. for 5 min |
| Ramp rate | 4° C. per min |
| 4$^{th}$ oven temperature | 270° C. for 15 min |
| Total run time | 59.50 min |

What is claimed is:

1. An isolated marine bacterium, Pseudomonas CH07, which is NRRL B-30604 that is used for degradation of several/different congeners of PCBs contained in Clophen A-50.

2. A bacterium as claimed in claim 1 wherein the degradation of PCBs mixture in Clophen A-50 is based on its unique properties.

3. A bacterium as claimed in claim 1 degrades non-ortho or mono-ortho chlorinated biphenyls (coplanar), ortho-substituted chlorinated biphenyls and sterically hindered chlorinated biphenyls.

4. A bacterium as claimed in claim 1 degrades most of the congeners present in Clophen A-50 either its single or multiple congeners.

5. A bacterium as claimed in claim 1 degrades the congeners of PCB are selected from tetra-chlorobiphenyls, pentachlorobiphenyls, hexachlorobiphenyls and heptachlorobiphenyls containing 4–7 chlorine atoms on the biphenyl ring, sterically hindered di, tri-ortho chlorinated biphenyls and coplanar congeners of PCB.

6. A bacterium as claimed in claim 1 is used to detoxify Clophen A-50 and its constituent congeners of PCB when present at or equal to 100 ppm level.

7. A bacterium as claimed in claim 1 is capable of degrading six sterically hindered di-ortho chlorinated biphenyls (cb-101, cb-97, cb-141, cb-138, cb-128 and cb-180).

8. A bacterium as claimed in claim 1 is capable of degrading two of the three most toxic coplanar PCBs in Clophen A-50.

9. A bacterium as claimed in claim 1 degrades the PCBs present in Clophen A-50 within a short period of 40 hours.

10. A bacterium as claimed in claim 1 wherein, 10 μl to 50 μl of the culture is used to degrade toxic PCBs present in Clophen A-50.

11. A bacterium as claimed in claim 1 degrades 20 to 100% of PCBs present in Clophen A-50.

12. A microbial process for the degradation of PCBs present in Clophen A-50, said process comprising culturing the marine bacterium, Pseudomonas CH07 and treating the PCBs with the bacterium for degrading congeners present in Clophen A-50.

13. A process as claimed in claim 12 wherein, Pseudomonas CH07 degrades non-ortho or mono-ortho chlorinated biphenyls (coplanar), ortho-substituted chlorinated biphenyls and sterically hindered chlorinated biphenyls PCBs present in Clophen A-50.

14. A process as claimed in claim 12 wherein, PCBs are degraded substantially within a short period of 40 hours.

15. A process as claimed in claim 12 wherein, the congeners of PCB degraded are selected from tetrachlorobiphenyls, pentachlorobiphenyls, hexachlorobiphenyls and hepta-chlorobiphenyls containing 4–7 chlorine atoms on the biphenyl ring, sterically hindered di, tri-ortho chlorinated biphenyls and coplanar congeners of PCB.

16. A process as claimed in claim 12 wherein, tetrachloro biphenyl in Clophen A-50 is degraded by this bacterium.

17. A process as claimed in claim 12 wherein, seven pentachloro biphenyl in Clophen A-50 are degraded.

18. A process as claimed in claim 12 wherein, four hexachlorobiphenyl in Clophen A-50 are degraded.

19. A process as claimed in claim 12 wherein, two heptachlorobiphenyl in Clophen A-50 are degraded.

20. A process as claimed in claim 12 wherein, the bacterium degrades the PCBs at a concentration ranging between 10 μl to 50 μl.

21. A process as claimed in claim 12 wherein, the bacterium degrades 20 to 100% of PCBs present in Clophen A-50.

22. A process as claimed in claim 12 wherein, said process is useful to detoxify Clophen A-50 and its constituent congeners of PCB when present at or equal to 100-ppm level.

23. A process as claimed in claim 12 wherein, the bacterium is isolated from marine environment and not altered genetically, and can be employed in situations at experimental pilot and at commercial scales, wherever there are marine conditions.

24. A process as claimed in claim 12 wherein, the bacterial strain is capable of degrading six sterically hindered di-ortho chlorinated biphenyls (cb-101, cb-97, cb-141, cb-138, cb-128 and cb-180).

25. A process as claimed in claim 12 wherein, two sterically hindered tri-ortho chlorinated biphenyls (cb-151 and cb-181) are degraded.

26. A process as claimed in claim 12 wherein, these sterically hindered congeners are degraded by this organism under marine condition.

27. A process as claimed in claim 12 wherein, different congeners of PCBs present in Clophen A-50, two congeners (CB-126, CB-181) get completely degraded.

28. A process as claimed in claim 12 wherein, cb-126 is completely degraded in about 40 hours.

29. A process as claimed in claim 12 wherein, the marine bacterium is the most potent for degradation of two of the three most toxic coplanar PCBs in Clophen A-50.

30. A process as claimed in claim 12 wherein, the organism is capable of degrading PCB congeners, cb-126 and cb-77 under marine condition.

31. A process as claimed in claim 12 wherein, coplanar PCB (3,3',4,4'-tetrachlorobiphenyl) is degraded very substantially within a short period of 40 hours.

* * * * *